United States Patent [19]
Harris et al.

[11] Patent Number: 5,395,640
[45] Date of Patent: Mar. 7, 1995

[54] METHOD OF PREPARING REDUCED FAT FOODS

[75] Inventors: Donald W. Harris; Jeanette A. Little, both of Decatur, Ill.

[73] Assignee: A.E. Staley Manufacturing Company, Decatur, Ill.

[21] Appl. No.: 918,862

[22] Filed: Jul. 30, 1992

Related U.S. Application Data

[63] Continuation-in-part of Ser. No. 746,381, Aug. 16, 1991, abandoned, and a continuation-in-part of Ser. No. 798,291, Nov. 26, 1991, abandoned, which is a continuation-in-part of Ser. No. 908,728, Jul. 6, 1992, which is a continuation of Ser. No. 578994, Sep. 6, 1990, abandoned, which is a continuation-in-part of Ser. No. 483,208, Feb. 20, 1990, abandoned.

[51] Int. Cl.⁶ .......................................... A23L 1/0522
[52] U.S. Cl. .................................... 426/573; 426/578; 426/658; 426/661; 426/603; 426/604; 426/804; 426/18; 426/28; 127/29; 127/32; 127/33; 127/36; 127/38; 127/39; 127/40; 127/58; 127/65; 127/69; 127/70; 127/71; 252/315.3
[58] Field of Search ............... 426/573, 578, 658, 661, 426/603, 604, 804, 18, 28; 127/29, 32, 33, 36, 38, 39, 40, 58, 65, 69–71; 252/315.3

[56] References Cited

U.S. PATENT DOCUMENTS

| | | | |
|---|---|---|---|
| 675,822 | 6/1901 | Duryea . | |
| 696,949 | 4/1902 | Duryea . | |
| 2,068,051 | 1/1937 | Canton | 426/578 |
| 2,131,064 | 9/1938 | Musher | 426/633 |
| 2,503,053 | 4/1950 | Kerr | 127/38 |
| 2,791,508 | 5/1957 | Rivoche | 426/573 |
| 2,805,995 | 9/1957 | Adelson | 252/33.6 |
| 2,978,446 | 4/1961 | Battista et al. | 260/212 |
| 3,023,104 | 2/1962 | Battista et al. | 99/1 |
| 3,067,067 | 12/1962 | Etheridge | 127/71 |
| 3,093,486 | 6/1963 | Krett et al. | 99/144 |
| 3,133,836 | 5/1964 | Winfrey et al. | 127/71 |
| 3,197,337 | 7/1965 | Schink | 127/28 |
| 3,219,483 | 11/1965 | Goos et al. | 127/28 |
| 3,351,489 | 11/1967 | Battista et al. | 127/32 |
| 3,370,840 | 3/1968 | Sugimoto et al. | 195/32 R |
| 3,532,602 | 10/1970 | Seidman | 195/31 |
| 3,556,942 | 1/1971 | Hathaway | 195/31 |
| 3,582,359 | 6/1971 | Horn | 426/573 |
| 3,586,536 | 6/1971 | Germino | 127/32 |
| 3,600,186 | 8/1971 | Mattson | 99/1 |
| 3,666,557 | 5/1972 | Jensen et al. | 127/32 |
| 3,671,269 | 6/1972 | Germino | 99/139 |
| 3,705,811 | 12/1972 | Yoshida et al. | 99/91 |
| 3,717,475 | 2/1973 | Germino | 99/134 |
| 3,730,840 | 5/1973 | Sugimoto et al. | 195/31 R |
| 3,830,697 | 8/1974 | Yoshida et al. | 195/31 R |
| 3,879,212 | 4/1975 | Yoshida et al. | 106/213 |
| 3,881,991 | 5/1975 | Kurimoto et al. | 195/31 R |
| 3,883,365 | 5/1975 | Forsberg | 127/60 |
| 3,928,062 | 12/1975 | Yamauchi | 127/60 |
| 3,962,465 | 6/1976 | Richter et al. | 426/48 |
| 3,986,890 | 10/1976 | Richter et al. | 127/38 |
| 4,009,291 | 2/1977 | Mitchell | 426/548 |
| 4,069,157 | 1/1978 | Hoover | 210/433 M |

(List continued on next page.)

FOREIGN PATENT DOCUMENTS 1016006 8/1977 Canada .
0052899 2/1982 European Pat. Off. .

(List continued on next page.)

OTHER PUBLICATIONS

Allmere et al., Derwent Abstract 93-174080 for SU 1736975, May 1992.

(List continued on next page.)

Primary Examiner—Joseph Golian
Attorney, Agent, or Firm—Arnold, White & Durkee

[57] ABSTRACT

A method of preparing reduced fat foods is provided which employs a fragmented, debranched amylopectin starch precipitate. A debranched amylopectin starch is precipitated and then fragmented to form an aqueous dispersion that is useful in replacing fat in a variety of food formulations. The debranched amylopectin starch can be derived from a starch which contains amylopectin, e.g. common corn starch and waxy maize starch, by gelatinizing the starch followed by treatment with a debranching enzyme, e.g. isoamylase or pullulanase and precipitation of the debranched starch.

26 Claims, 1 Drawing Sheet

U.S. PATENT DOCUMENTS

| | | | |
|---|---|---|---|
| 4,143,163 | 3/1979 | Hutchison | 426/96 |
| 4,143,174 | 3/1979 | Shah et al. | 426/570 |
| 4,192,900 | 3/1980 | Cheng | 426/578 |
| 4,199,374 | 4/1980 | Dwivedi | 127/60 |
| 4,209,503 | 6/1980 | Shah et al. | 424/49 |
| 4,263,334 | 4/1981 | McGinley | 426/573 |
| 4,276,312 | 6/1981 | Merritt | 426/96 |
| 4,291,065 | 9/1981 | Zobel | 426/549 |
| 4,305,964 | 12/1981 | Moran et al. | 426/99 |
| 4,308,294 | 12/1981 | Rispoli et al. | 426/564 |
| 4,423,084 | 12/1983 | Trainor et al. | 426/589 |
| 4,477,480 | 10/1984 | Seidel | 426/578 |
| 4,492,714 | 1/1985 | Cooper | 426/602 |
| 4,492,714 | 1/1985 | Cooper et al. | 426/602 |
| 4,510,166 | 4/1985 | Lenchin et al. | 426/565 |
| 4,533,254 | 8/1985 | Cook et al. | 366/176 |
| 4,536,408 | 8/1985 | Morehouse et al. | 426/250 |
| 4,551,177 | 11/1985 | Trubiano | 106/210 |
| 4,560,559 | 12/1985 | Ottenburg | 426/19 |
| 4,587,131 | 5/1986 | Bodor | 426/603 |
| 4,587,131 | 5/1986 | Bodor et al. | 426/603 |
| 4,591,507 | 5/1986 | Bodor | 426/604 |
| 4,591,507 | 5/1986 | Bodor et al. | 426/604 |
| 4,643,773 | 2/1987 | Day | 127/30 |
| 4,670,272 | 6/1987 | Chen | 426/573 |
| 4,726,957 | 2/1988 | Lacourse | 426/578 |
| 4,728,526 | 3/1988 | Avera | 426/633 |
| 4,787,939 | 11/1989 | Barker | 127/37 |
| 4,810,307 | 3/1989 | Caton | 127/63 |
| 4,810,646 | 3/1989 | Jamas | 435/101 |
| 4,814,195 | 3/1989 | Yokohama | 426/633 |
| 4,828,868 | 5/1989 | Lasdon | 426/633 |
| 4,832,977 | 5/1989 | Avera | 426/633 |
| 4,869,919 | 9/1989 | Lowery | 426/604 |
| 4,885,180 | 12/1989 | Cochran | 426/241 |
| 4,886,678 | 12/1989 | Chiu | 426/578 |
| 4,911,946 | 3/1990 | Singer | 426/658 |
| 4,911,946 | 3/1990 | Singer et al. | 426/658 |
| 4,917,915 | 4/1990 | Cain | 426/573 |
| 4,917,915 | 4/1990 | Cain et al. | 426/573 |
| 4,937,091 | 6/1990 | Zallie | 426/582 |
| 4,937,091 | 6/1990 | Zallie et al. | 426/582 |
| 4,942,055 | 7/1990 | Avera | 426/633 |
| 4,948,615 | 8/1990 | Zallie | 426/573 |
| 4,954,178 | 9/1990 | Caton | 127/32 |
| 4,957,750 | 9/1990 | Cochran | 426/19 |
| 4,962,094 | 10/1990 | Jamas | 514/54 |
| 4,971,723 | 11/1990 | Chiu | 252/315.3 |
| 4,981,709 | 1/1991 | Furcsik et al. | 426/565 |
| 5,051,271 | 9/1991 | Iyengar et al. | 426/658 |
| 5,094,872 | 3/1992 | Furcsik et al. | 426/578 |
| 5,104,674 | 4/1992 | Chen et al. | 426/573 |
| 5,110,612 | 5/1992 | Quarles | 426/573 |
| 5,131,953 | 7/1992 | Kasica | 127/65 |
| 5,137,742 | 8/1992 | Bakal et al. | 426/589 |
| 5,147,665 | 9/1992 | Furcsik | 426/19 |
| 5,192,569 | 3/1993 | McGinley et al. | 426/96 |
| 5,192,569 | 3/1993 | McGinley et al. | 426/96 |

FOREIGN PATENT DOCUMENTS

| | | |
|---|---|---|
| 0237120 | 9/1987 | European Pat. Off. |
| 0298561 | 1/1989 | European Pat. Off. |
| 0327120 | 8/1989 | European Pat. Off. |
| 0327288 | 8/1989 | European Pat. Off. |
| 0340035 | 11/1989 | European Pat. Off. |
| 0367064 | 5/1990 | European Pat. Off. |
| 0372184 | 6/1990 | European Pat. Off. |
| 0387940 | 9/1990 | European Pat. Off. |
| 0420314 | 4/1991 | European Pat. Off. |
| 0420315 | 4/1991 | European Pat. Off. |
| 0427312 | 5/1991 | European Pat. Off. |
| 0430329 | 6/1991 | European Pat. Off. |
| 0443844 | 8/1991 | European Pat. Off. |
| 0470870 | 2/1992 | European Pat. Off. |
| 0480433 | 4/1992 | European Pat. Off. |
| 0486936 | 5/1992 | European Pat. Off. |
| 110957 | of 1897 | Germany. |
| 142646A | 7/1980 | German Dem. Rep. |
| 161178A | 5/1985 | German Dem. Rep. |
| 60-160833 | 8/1985 | Japan. |
| 3-296501 | 12/1991 | Japan. |
| 4-46901 | 2/1992 | Japan. |
| 2247242 | 2/1992 | United Kingdom. |
| WO87/04465 | 7/1987 | WIPO. |
| 89/12403 | 12/1989 | WIPO. |
| WO90/00010 | 1/1990 | WIPO. |
| WO90/06343 | 6/1990 | WIPO. |
| 90/63436 | 6/1990 | WIPO. |
| 90/15147 | 12/1990 | WIPO. |
| 91/01091 | 2/1991 | WIPO. |
| WO91/01092 | 2/1991 | WIPO. |
| 91/07106 | 5/1991 | WIPO. |
| WO91/12728 | 9/1991 | WIPO. |
| 9202614 | 2/1992 | WIPO. |
| WO92/21703 | 12/1992 | WIPO. |

OTHER PUBLICATIONS

Stute R., Hydrothermal modification of Starches: The Difference between Annealing and Heat/Moisture--Treatment, Starch 44 (1992) Nr. 6, 205–214.

"Low fat ground beef patties", brochure, A. E. Staley Mfg. Co. (Oct. 1991).

(List continued on next page.)

OTHER PUBLICATIONS

"Low-fat pork sausage patty", formula sheet CFSF7 196211, A. E. Staley Mfg. Co.

"Solve tough process filtration problems with Ceraflo ceramic systems", technical bulletin, lit. No. SD113, Feb. 1989 89-418, Milliport Corp. (1989).

"Staley Formulation of Food Starch-Modified", new product review presented to U.S. Food and Drug Administration by A. E. Staley Mfg. Co. (Nov. 1990).

Ambler, "Centrifugation", Handbook of Separation Techniques for Chemical Engineers, pp. 4-60 to 4-88 (McGraw Hill 1988).

BeMiller, "Gums", Encyclopedia of Food Science & Technology, vol. 2, pp. 1338-1344 (John Wiley & Sons 1992).

Bouchard et al, "High performance liquid chromatographic monitoring of carbohydrate fractions in partially hydrolyzed corn starch", J. Agric. Food Chem., vol. 36, pp. 1188-1192 (1988).

Duxbury, "Modified food starches partially replace fats, oils & provide smooth texture", Food Processing, pp. 86-88 (Nov. 1990).

Duxbury, "Pre-hydrated gums eliminate lumping, long hydration times," Food Processing, pp. 44-48 (Jun. 1992).

Dziezak, "Emulsifiers: the interfacial key to emulsion stability", Food Technology, vol. 42, No. 10, pp. 171-186 (Oct. 1988).

Dziezak, "Membrane separation technology offers processors unlimited potential", Food Technology, pp. 108-113 (Sep. 1990).

Falkiewicz, "Avicel in suspensions—dispersion, rheology and colloid science", Soap, Cosmetics, Chemical Specialties, pp. 27-34 (Apr. 1979).

Faulkner et al, "Size reduction", Encyclopedia of Chemical Technology, vol. 21, pp. 132-162 (Kirk Othmer eds., John Wiley & Sons, 1983).

Ghiasi et al, "Effects of flour components and dough ingredients on starch gelatinization", Cereal Chemistry, vol. 60, No. 1, pp. 58-61 (1983).

Giese, "Developing low-fat meat products", Food Technology, pp. 100-108 (Apr. 1992).

Kerr, Chemistry and Industry of Starch, 2d ed., pp. 564-567 (Academic Press 1950).

Klinkowski, "Ultrafiltration", Encyclopedia of Chemical Technology, vol. 23, pp. 439-461 (Kirk-Othmer, eds., John Wiley & Sons, 3d ed. 1983).

Knightly, "The evolution of softeners and conditioners used in baked foods", The Bakers Digest, pp. 64-75 (Oct. 1973).

Koizumi et al, "High performance anion-exchange chromatography of homogenous D-gluco oligosaccharides and polysaccharides (polymerization degree equal to or greater that 50) with pulsed amphoteric detection", Journal of Chromatography, vol. 46, pp. 364-373 (1989).

Krog, "Functions of emulsifiers in food systems", J. Am. Oil Chemists' Society, vol. 54, pp. 124-131 (1978).

Larsson et al, "Annealing of starch at an intermediate water content", Starch/Starke, vol. 43, No. 6, pp. 227-231 (Jun. 1991).

Lavanchy et al, "Centrifugal separation", Encyclopedia of Chemical Technology, vol. 5, pp. 194-233 (Kirk-Othmer, eds., John Wiley & Sons, 3d ed., 1979).

Luu et al, "Model structure for liquid water, etc.", Travaux de la Societe de Pharmacie de Montpellier, vol. 41, No. 3, pp. 203-212 (1981) (Translation attached).

Manley, Technology of Biscuits, Crackers and Cookies, pp. 335-347 (Ellis Horwood 1983).

Mason, "Chemistry with ultrasound", Critical Reports on Applied Chemistry, vol. 28, pp. 1-26, 91-98, 159-187 (Elsevier Science Publishers 1990).

Matthews, Legumes: Chemistry, Technology, and Human Nutrition, pp. 226-229 (Marcel Dekker 1989).

Matz, Cookie and Cracker Technology, pp. 163-167 (AVI Publishing 1968).

Mussulman et al, "Electron microscopy of unmodified and acid-modified corn starches", Cereal Chemistry, vol. 45, pp. 162-171 (1968).

Nara et al, "Study on relative crystallinity of moist potato starch", Starke/Starch, vol. 30, pp. 111-114 (1978).

Orr, "Size measurement of particles", Encyclopedia of Chemical Technology, vol. 21, pp. 106-131 (Kirk Othmer eds., John Wiley & Sons, 1983).

Pancoast et al, Handbook of Sugars, pp. 157-287 (AVI Publishing 1980).

(List continued on next page.)

OTHER PUBLICATIONS

Patterson, Hydrogenation of Fats and Oils, pp. 44–48, 173–182, 291–304 (Applied Science Publishers, 1983).

Paul et al, "Membrane technology", Encyclopedia of Chemical Technology, vol. 15, pp. 92–131 (Kirk-Othmer, eds., John Wiley & Sons, 3d ed. 1981).

Pszczola, "Oat-bran-based ingredient blend replaces fat in ground beef and pork sausage", Food Technology, pp. 60–66 (Nov. 1991).

Reuther et al, "Structure of maltodextrin gels—a small angle X-ray scattering study", Colloid and Polymer Science, vol. 261. pp. 271–276 (1983).

Richards, Breads, Rolls and Sweet Doughs, pp. 92–95 (Peacock Business Press, 1973).

Richardson, "Molecular mobilities of instant starch gels determined by oxygen-17 and carbon-14 nuclear magnetic resonance", Journal of Food Science, vol. 53, pp. 1175–1180 (1988).

Savage et al, "Effects of certain sugars and sugar alcohols on the swelling of cornstarch granules", Cereal Chemistry, vol. 55, No. 4, pp. 447–454 (1978).

Spies et al, "Effect of sugars on starch gelatinization", Cereal Chemistry, vol. 59, No. 2, pp. 128–131 (1982).

Stadelman et al, Egg and Poultry Meat Processing, pp. 52–63 (Ellis Horwood 1988).

Taki, "Functional ingredient blend produes low-fat meat products to meet consumer expectations", Food Technology, pp. 70–74 (Nov. 1991).

J. Jane et al., "Preparation and Properties of Small-Particle Corn Starch, *Cereal Chemistry*, vol. 69, pp. 280–283 (1992).

"Paselli SA2; The Natural Alternative to Fats and Oils" (AVEBE b.a., Foxhol, Holland, Ref. No. 05.12.31.167 EF).

T. H. Applewhite, "Fats and Fatty Oils", *Encyclopedia of Chemical Technology*, vol. 9, pp. 795–831 (Kirk-Othmer, eds., John Wiley & Sons, N.Y., N.Y., 3d ed., 1980).

R. L. Whistler et al., *Starch: Chemistry and Technology*, pp. 25–35 (Academic Press, Inc., New York, N.Y., 1984).

H. Reuter, "Homogenization", *Encyclopedia of Food Science*, pp. 374–376 (M. S. Peterson and A. H. Johnson, eds., AVI Publ. Co., Westport, Conn. 1978).

L. H. Rees and W. D. Pandolfe, "Homogenizers", *Encyclopedia of Food Engineering*, pp. 467–472 (C. W. Hall et al., eds., AVI Publ. Co., Westport, Conn., 1986).

W. C. Griffin, "Emulsions", *Encyclopedia of Chemical Technology*, vol. 8, pp. 900–930 (Kirk-Othmer, eds., John Wiley & Sons, N.Y., N.Y., 3d ed., 1979).

U.S. Ser. No. 07/918,952, filed Jul. 30, 1992.

U.S. Ser. No. 07/746,432, filed Aug. 16, 1991.

Teot, "Resins, water-soluble", Encyclopedia of Chemical Technology, vol. 20, pp. 207–230 (John Wiley & Sons 1982).

Trout, "Pasteurization", Encyclopedia of Food Science, pp. 600–604 (Peterson et al eds., AVI Publ. Co., 1978).

Wang, "Meat processing I", Encyclopedia of Food Engineering, pp. 545–557 (AVI Publishing 1986).

White et al, "Predicting gelatinization temperatures of starch/sweetener systems for cake formulations by differential scanning calorimetry. I. Development of model." Cereal Foods World, vol. 35, No. 8, pp. 728–731 (Aug. 1990).

Wilhoft, "Recent developments on the bread staling problem", The Bakers Digest, pp. 14–20 (Dec. 1973).

Wurzburg, Modified Starches: Properties and Uses, pp. 18–23, 38–40, 244–245, and 251–252 (CRC Press, 1986).

Yamaguchi et al, "Electron microscopic observations of waxy maize starch", Journal of Ultrastructure Research, vol. 69, pp. 249–261 (1979).

Tegge, "Produkte der sauren Stärkehydrolyse", Die Stärken, pp. 244–246 (1981). (English translation).

"Food Labelling; Serving Sizes", 55 Fed. Reg. 29517 (1990).

"Food Labelling; Definitions of the Terms Cholesterol Free, Low Cholesterol, and Reduced Cholesterol", 55 Fed. Reg. 29456 (1990).

I. Larrson and A. Eliasson, "Annealing of Starch at an Intermediate Water Content", *Starch*, vol. 43, No. 6, pp. 227–231 (Jun. 1991).

D. Sievert et al., "Enzyme-Resistant Starch. I. Characterization and Evaluation by Enzymatic, Thermoanalytical, and Microscopic Methods", *Cereal Chemistry*, vol. 66, pp. 342–347 (1989).

J. L. Lane et al., "Structure Studies of Amylose-V Complexes and Retrograded Amylose by Action of Alpha Amylases, and A New Method for Preparing Amylodextrins", *Carbohydrate Research*, vol. 132, pp. 105–118 (1984).

P. L. Russell et al., "Characterisation of Resistant (List continued on next page.)

OTHER PUBLICATIONS

Starch from Wheat and Maize", *Journal of Cereal Science*, vol. 9, pp. 1–15 (1989).

R. J. Swientek, "Microfluidizing Technology Enhances Emulsion Stability", *Food Processing*, pp. 152–153 (Jun. 1990).

*RANNIE High Pressure Laboratory Homogeniser*, a service manual (Rannie a/s, Roholmsvej 8, DK-2620 Albertslund, Denmark).

"Fat-Sparing Starch Can Replace 100% Fat/Oil for 96% Calorie Reduction", *Food Processing*, p. 38 (Dec. 1990).

W. A. Atwell et al., "Characterization of Quinoa Starch", *Cereal Chemistry*, vol. 60, pp. 9–11 (1982).

"New Generation of Foods With Reduced Fat", *Food Engineering*, pp. 23 and 26 (Jan. 1990).

O. A. Battista et al., "Colloidal Macramolecular Phenomena. Part II. Novel Microcrystals of Polymers", *Journal of Applied Polymer Science*, vol. 11, pp. 481–498 (1967).

N. Z. Erdi et al., "Rheological Characteristics of Polymeric Microcrystal–Gels", *Journal of Colloid and Interface Science*, vol. 28, pp. 36–47.

"NEPOL Amylose", Market Development Bulletin No. 101, A. E. Staley Manufacturing Company.

O. A. Battista et al., "Microcrystalline Cellulose", *Industrial and Engineering Chemistry*, vol. 54, pp. 20–29 (1962).

"AVICEL RC 581 Technical Bulletin", Bulletin No. RC–11, FMC Corporation, Marcus Hook, Pa., 11/69–1M.

"AVICEL Microcrystalline Cellulose; The Non–Caloric Ingredient", a bulletin of American Viscose Corporation, Marcus Hook, Pa. (later a division of FMC Corporation).

"AVICEL RC–591 in Foods", Bulletin No. RC–22, FMC Corporation, Marcus Hook, Pa. (May 1972).

"AVICEL RC in Bakery Products", Bulletin No. RC–35, FMC Corporation, Marcus Hook, Pa.

"AVICEL RC in Canned Foods", Bulletin No. RC–31, FMC Corporation, Marcus Hook, Pa.

"AVCEL Pricing", a bulletin apparently of American Viscose Corporation, Marcus Hook, Pa. (later a division of FMC Corporation).

"C9–112 Microcrystalline Starch", a product bulletin of A. E. Staley Manufacturing Company.

A. H. Young, "Evaluation of Microcrystals Prepared From MIRA–QUIK C in Pilot Plant Spray Dried in the Presence of Sodium Carboxymethylcellulose (C9–112)". Project Report RD 73–17 of A. E. Staley Manufacturing Company.

G. R. Sanderson, "Polysaccharides in Foods", *Food Technology*, pp. 50–57 and 83 (Jul. 1981).

"Gums and Starches Bulk Up Low–Cal Foods", *Food Engineering* (Jan. 1990).

"STA–SLIM Starches", a technical data sheet published by A. E. Staley Manufacturing Company, TDS 507 096060.

"Reduced–Oil Salad Dressings", a technical publication of A. E. Staley Manufacturing Company.

"STELLAR Fat Replacer", a technical data sheet published by A. E. Staley Manufacturing Company, TDS 513 192250.

"STELLAR Fat Replacer; Structure", a technical information bulletin published by A. E. Staley Manufacturing Company, TIB 29 195060.

"STELLAR Fat Replacer; Handling, Storage, and Preparation", a technical information bulletin published by A. E. Staley Manufacturing Company, TIB 28 195060.

E. Dickinson, "Particle Gels", *Chemistry & Industry*, pp. 595–599 (Oct. 1990).

S. Lansky et al., "Properties of the Fractions and Linear Subfractions from Various Starches", *J. Am. Chem. Soc.*, vol. 71, pp. 4066–4075 (1949).

R. L. Whistler and C. Johnson, "Effect of Acid Hydrolysis on the Retrogradation of Amylose", *Cereal Chemistry*, vol. 25, pp. 418–424 (1948).

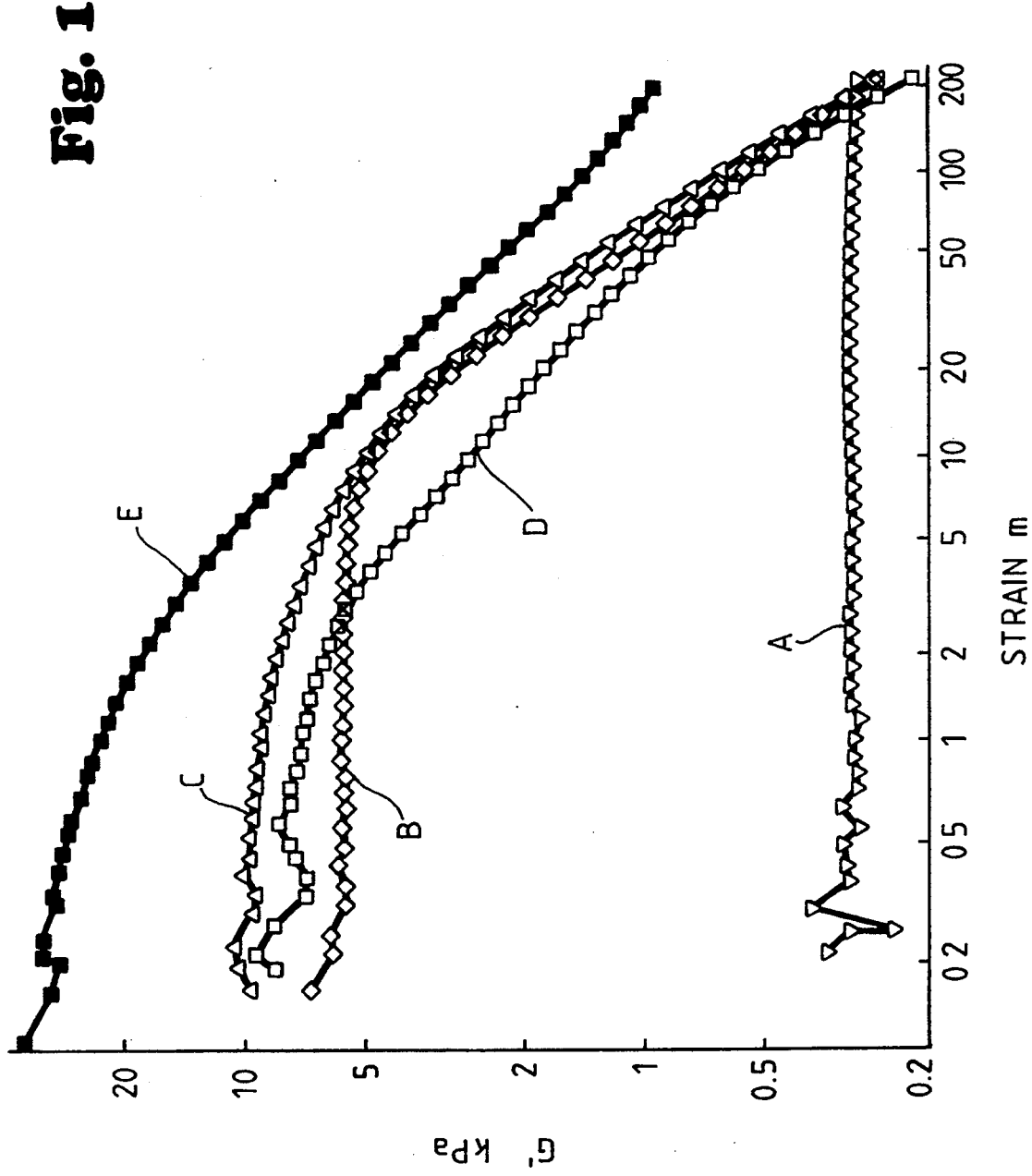

METHOD OF PREPARING REDUCED FAT FOODS

CROSS-REFERENCE TO RELATED APPLICATIONS

This application is a continuation-in-part of U.S. application Ser. No. 07/746,381, filed Aug. 16, 1991, and U.S. application Ser. No. 07/798,291, filed Nov. 26, 1991, the disclosure of each of which are incorporated herein by reference, both applications now abandoned.

FIELD OF THE INVENTION

This invention relates to food formulations in which at least a portion of the fat and/or oil is replaced by a carbohydrate.

BACKGROUND OF THE INVENTION

U.S. Pat. No. 4,510,166 (Lenchin et al.) discloses converted starches having a DE less than 5 and certain paste and gel characteristics which are used as a fat and/or oil replacement in various foods, including ice cream and mayonnaise. The converted starches are described as dextrins, acid-converted starches (fluidity starches), enzyme-converted starches and oxidized starches. It is also disclosed that if the converted starches are not rendered cold-water soluble by the conversion, they are pregelatinized prior to use or cooked during use.

A product bulletin entitled "Paselli SA2; The Natural Alternative to Fats and Oils" (AVEBE b.a., Foxhol, Holland, Ref. No. 05.12.31. 167 EF) discloses the use of a low-DE-hydrolysate (DE less than 3) made from potato starch as a replacement for fifty percent of the fat with an amount of the low-DE-potato starch hydrolysate plus water (starch hydrolysate at 28% dry solids) equal to the amount of fat replaced.

U.S. Pat. Nos. 3,962,465 (Richter et al.) and 3,986,890 (Richter et al.) disclose the use of thermoreversible gels of a starch hydrolysate (formed by enzymatic hydrolysis) as a substitute for fat in a variety of foods, including cake creams and fillings, mayonnaise and remoulades, cream cheeses and other cheese preparations, bread spreads, pastes, meat and sausage products, and whipped cream.

U.S. Pat. No. 4,971,723 (Chiu) discloses partially debranched starch prepared by enzymatic hydrolysis of the α-1,6-D-glucosidic bonds of the starch, comprising amylopectin, partially debranched amylopectin and up to 80% by weight, short chain amylose and that the partially debranched starch is useful in a variety of ways depending upon the degree of debranching. It is disclosed that a waxy maize starch (or other waxy starch) can be partially debranched (i.e. to 25% to 70% short chain amylose) to yield sufficient short chain amylose to form a thermally reversible gel in an aqueous starch suspension. It is further disclosed that the same degree of debranching of waxy starches is preferred for lending a fat-like, lubricating texture to an aqueous starch dispersion.

SUMMARY OF THE INVENTION

In one aspect, this invention relates to a food formulation having a reduced level of fat and/or oil comprising a mixture of a foodstuff and a fragmented, debranched amylopectin starch precipitate as a replacement for at least a substantial portion of the fat and/or oil of said food formulation, said fragmented, debranched amylopectin starch precipitate being capable of forming a particle gel in aqueous dispersion.

In another aspect, this invention relates to a method of formulating a food containing a fat and/or oil ingredient comprising replacing at least a substantial portion of said fat and/or oil ingredient with a fragmented, debranched amylopectin starch precipitate being capable of forming a particle gel in aqueous dispersion.

By "fragmented, debranched amylopectin starch precipitate" is meant a starch material comprised of amylopectin which has been subjected to enzymatic debranching followed by precipitation and then mechanical disintegration of the precipitate into fragments. The debranching and disintegration will be sufficient to produce a precipitate which will form an aqueous dispersion having the characteristics of a particle gel.

In another aspect, this invention relates to a method of making a composition of matter useful in replacing fat and/or oil in a food formulation comprising physically fragmenting a minor amount of a debranched amylopectin starch precipitate in a major amount of an aqueous liquid, the degree of said physically fragmenting being sufficient to form a particle gel of said composition.

In another aspect, this invention relates to an aqueous dispersion useful as a replacement for fats and/or oils comprising a major amount by weight of water and a minor amount by weight of a fragmented, debranched amylopectin starch precipitate, the degree of debranching and fragmentation of said precipitate being sufficient to form a particle gel of said composition.

The terms "foodstuff" and "food", as used herein, are intended to broadly cover nutritional and/or functional materials that are ingested by humans in the course of consuming edible fare. The term "fats and/or oils" is intended to broadly cover edible lipids in general, specifically the fatty acid triglycerides commonly found in foods. The terms thus include solid fats, plastic shortenings, fluid oils, and the like. Common fatty acid triglycerides include cottonseed oil, soybean oil, corn oil, peanut oil, canola oil, sesame oil, palm oil, palm kernel oil, menhaden oil, whale oil, lard, and tallow. The technology of fats and/or oils is described generally by T. H. Applewhite, "Fats and Fatty Oils", *Encyclopedia of Chemical Technology*, Vol. 9, pp. 795–831 (Kirk-Othmer, eds., John Wileys Sons, Inc., New York, N.Y., 3d ed., 1980), the disclosure of which is incorporated by reference.

The use of the terms "major" and "minor" in context together in this specification is meant to imply that the major component is present in a greater amount by weight than the minor component, and no more nor less should be inferred therefrom unless expressly noted otherwise in context.

BRIEF DESCRIPTION OF THE DRAWINGS

FIG. 1 shows the dynamic elastic modulus (G') in kilo pascals as a function of strain (m) for fragmented, debranched amylopectin starch precipitates at 25% precipitate solids having different degrees of debranching and for a commercially available partially hydrogenated shortening.

DETAILED DESCRIPTION OF THE INVENTION

The fragmented, debranched amylopectin starch precipitate is made by the sequential steps of debranching, precipitation, and fragmentation of a starch material containing amylopectin. Starch is generally comprised of a highly-branched glucan having α-1,4 and α-1,6 linkages, denominated amylopectin, and a substantially linear glucan, having almost exclusively α-1,4 linkages, denominated amylose, Methods of determining the amounts of each are referenced in R. L. Whistler et al., *Starch: Chemistry and Technology*, pp. 25–35 (Academic Press, Inc., New York, N.Y., 1984), the disclosure of which is incorporated by reference. Starches having a major proportion (i.e. at least 50% by weight) of amylopect, in are preferred and examples of these include the common non-mutant starches of cereals, tubers and legumes, e.g. corn, wheat, rice, potato and tapioca, pea and mutant varieties comprised of a major proportion of amylopectin, e.g. waxy maize. Common corn starch and waxy maize starch, both of which are examples of starches containing less than 40% amylose, are useful herein. However, starches containing a major amount of amylose (e.g. 50% to 75% by weight) are also useful and may be preferred depending upon the precise properties desired in the final product. Examples of such starches from high amylose corn include HI-SET® C and HYLON TM (each about 55% amylose by weight) and HYLON TM VII (about 70% amylose by weight), all available from National Starch and Chemical Corporation, Bridgewater, N.J.

In certain embodiments, the starch consists essentially of amylopectin. In such embodiments, the starch employed is from a mutant variety of native starch which consists essentially of amylopectin or is amylopectin derived from a native starch variety containing both amylose and amylopectin. Methods for the fractionation of amylose and amylopectin from native starch are disclosed in, for example, U.S. Pat. No. 3,067,067 (Etheridge).

If the starch chosen as a starting material is not in pre-gelatinized or instant form, the starch must be gelatinized or pasted prior to debranching. The gelatinization or pasting process disrupts, at least in substantial part, the associative bonding of the starch molecules in the starch granule. This permits the enzyme to access to the molecule to more easily and uniformly debranch the amylopectin molecules. This disruption is accomplished by heating a slurry of the starch to a sufficient temperature for a sufficient length of time depending upon the inherent resistance of the particular starch to gelatinization and the amount of moisture present in the slurry. The slurry will typically be comprised of a major amount of water (i.e. at least 50% by weight) and a minor amount of the starch starting material (i.e. less than about 50% by weight). Preferably, the starch slurry will contain at least about 5% starch, typically between about 10% to about 25% starch. The pH of the slurry will generally be substantially neutral, i.e. from about 3.5 to about 9 and more preferably from about 6 to 8, to minimize hydrolysis of the starch molecules. The time, temperature, slurry solids and pH should be optimized to gelatinize the starch, yet minimize hydrolysis of the starch.

The appropriate temperature, pressure and period of treatment needed to provide a starch paste is preferably obtained by processing aqueous starch slurries in equipment commonly known in the art as steam injection heaters or jet cookers. In such equipment, superatmospheric steam is injected and mixed with a water slurry of starch in a throat section of a jet. Upon contact with the injected steam, the starch granules are uniformly and thermally treated under turbulent conditions whereupon the starch granules are gelatinized and solubilized. Examples of steam injection heaters wherein the temperature, pressure and feed rate can be regulated to provide the desired starch pastes are disclosed in U.S. Pat. Nos. 3,197,337; 3,219,483; and 3,133,836. More uniformly solubilized starch pastes are obtained by use of the steam injection heater in combination with a holding zone such as coiled tubing or a pressurized tank constructed to minimize liquid channeling. Other pasting equipment,. e.g. heat exchangers, homogenizers, cookers, rotators, sizeometer cookers, kettle cookers, etc., may be employed provided the pasting conditions can be adequately maintained.

The gelatinized starch is then treated with a debranching enzyme, i.e. an enzyme capable of hydrolyzing the 1,6-glucosidic bond of amylopectin without significant capability of hydrolyzing the 1,4-glucosidic bond. Enzymes from a variety of sources are capable of debranching amylopectin. U.S. Pat. No. 3,370,840 (Sugimoto et al.) describes sources of debranching enzymes, the disclosure of which is incorporated herein by reference. Examples of useful enzymes include pullulanases derived from bacteria of the genus Aerobacter (e.g. E.C. 3.2.1.41 pullulan 6-glucanohydrolase) and isoamylases derived from bacteria of the genus Pseudomonas (e.g. E.C. 3.2.1.68 glycogen 6-glucanohydrolase). Particularly useful enzymes include thermostable enzymes, e.g. thermostable pullulanases as disclosed in PCT Publ. No. WO 92/02614, published Feb. 20, 1992, the disclosure of which is incorporated by reference, and which are obtained from members of the genus Pyrococcus. The debranching enzyme may be in solution during debranching or it may be immobilized on a solid support.

The debranching enzyme preparation should be as specific as possible for the hydrolysis of the 1,6-glucosidic bond of amylopectin and amylose. Thus, the enzyme preparation, if it contains a mixture of enzymes, is preferably essentially free of enzymes capable of hydrolyzing α-1,4-glucosidic bonds. Minimizing hydrolysis of α-1,4-glucosidic bonds will help to minimize the amounts of dextrose and soluble oligomers produced during debranching. Because these soluble saccharities are not believed to contribute to the functionality of the debranched material, minimizing their production will enhance the yield of functional material.

The debranching enzyme is allowed to act upon the solubilized starch containing amylopectin. The optimum concentration of enzyme and substrate in the debranching medium will, in general, depend upon the level of activity of the enzyme which, in turn, will vary depending upon the enzyme source, enzyme supplier and the concentration of the enzyme in commercial batches. When the isoamylase E.C. 3.2.1.68, derived from Pseudomonas amyloderamosa, available from Sigma Chemical Co., St. Louis, Mo., is employed, typical conditions include the treatment of a starch solution at 5% to 30% by weight starch solids with about 50 units of enzyme per gram of starch for a period of about 48 hours to obtain substantially complete debranching.

The optimum pH and temperature of the debranching medium will also depend upon the choice of enzyme. The debranching medium may, in addition to the water used to solubilize the starch, contain buffers to ensure that the pH will be maintained at an optimum level throughout the debranching. Examples of useful buffers include acetates, citrates, and the salts of other weak acids. With the isoamylase described above, the pH is preferably maintained at about 4.0 to 5.0 and the temperature from about 40° C. to about 50° C. With the thermostable pullulanase described above, the pH is preferably maintained between 5 and 7 and the optimum temperature should be between 85° C. and 115° C.

The debranching is allowed to proceed until the desired degree of debranching has been obtained. The precise degree of debranching needed to obtain the desired particle gel of the debranched amylopectin starch may vary depending upon the source of the starch and the precise properties desired in the resulting gel. Preferably, the degree of debranching is sufficient to convert more than about 80% of the amylopectin in the starch to short chain amylose and, more preferably, at least about 90% of the amylopectin. In preferred embodiments, essentially all of the amylopectin is converted to short chain amylose. The amount of short chain amylose can be measured by gel permeation chromatography as set forth in U.S. Pat. No. 4,971,723, wherein short chain amylose is calculated from the relative area of the peak obtained within the molecular weight range of 500 to 20,000. Thus, preferably less than 20% of the amylopectin that was originally present will be present as molecular species having a molecular weight in excess of 20,000 g/mol, and most preferably, essentially no amylopectin having a molecular weight in excess of 20,000 g/mol will remain. (It should be noted that if amylose is present, at least a portion thereof may be debranched to produce molecules above the 20,000 g/mol cut-off and molecules below the 20,000 g/mol cut-off. To measure how much of the material eluting between 500 g/mol and 20,000 g/mol is debranched amylopectin and how much is debranched amylose, it may be necessary to fractionate the starting starch into its amylose and amylopectin fractions and then debranch and elute each fraction separately.)

It has been found, as described more fully below, that when waxy maize starch was debranched, precipitated and then fragmented, a degree of debranching of only about 57% resulted in an aqueous dispersion that displayed the rheological characteristics of a polymer gel. However, when the debranching was allowed to proceed to 69% and 85%, an aqueous dispersion of the fragmented precipitate displayed rheological properties characteristic of a particle gel. When the degree of debranching was substantially 100%, the fragmented precipitate displayed rheological properties even more closely resembling a particle gel, and in fact, which bore a remarkable resemblance to a commercially available plastic fat, i.e. CRISCO brand shortening, a product of Procter and Gamble, Cincinnati, Ohio.

After the desired degree of debranching is obtained, debranching enzyme in solution is deactivated, e.g. by heating to denature the enzyme. If an immobilized enzyme is employed, the contact time of the solubilized starch is adjusted so that the starch is removed from the enzyme when the desired degree of debranching is obtained. The debranching medium may be concentrated by removal of water therefrom, e.g. by evaporation, to facilitate precipitation. The debranching medium may also be treated to remove impurities therefrom. Treatment with, for example, activated carbon will remove residual proteins and lipids that may contribute to off-flavors and/or colors.

The solution of debranched starch is then allowed to form a precipitate. Generally, the solution will be cooled, e.g. to ambient temperature, to reduce the solubility of the debranched starch therein. The solution will typically be allowed to stand until substantial equilibrium is achieved between the supernatant and the precipitate. The precipitate can be isolated from the supernatant, e.g. by centrifugation, prior to fragmentation, but isolation from the supernatant is not necessary to form a useful product.

Heating (e.g. to about 70° C.) of the precipitate while in contact with a liquid medium (e.g. the supernatant from original precipitation and/or fresh water following isolation of the precipitate from tile supernatant) to dissolve at least a portion of the precipitate and then reprecipitation by cooling of the suspension/solution can also be employed. This reprecipitation tends to make the precipitate resistant to melting or dissolving when an aqueous dispersion of the fragmented precipitate is exposed to heat, e.g. in a pasteurization step. In general, the higher the temperature to which the precipitate in the liquid medium is heated (and thus the greater the amount of precipitate that is redissolved), the higher the temperature at which the resulting aqueous dispersion of fragmented precipitate will be stable. Repetition of the dissolving and reprecipitation also tends to improve the temperature stability of the resulting aqueous dispersion.

It is also advantageous to heat the precipitate to redissolve a substantial portion of the low melting polysaccharides and then treat the heated suspension of precipitate with acid or enzyme to hydrolyze soluble polysaccharides in the solution. (It may also be advantageous to filter the slurry while hot to remove soluble polysaccharides or their hydrolysates.) The dissolving and reprecipitation steps alone improve the stability of the aqueous dispersion by increasing the amount of the fragmented precipitate which remains as insoluble fragments in an aqueous dispersion that is exposed to heat. Further, a slow rate of heating and/or cooling (e.g. from about 0. 005° C./min. to about 0.5° C./min. for each) may be advantageous. However, the remaining soluble fraction of the precipitate can associate to form relatively large particles that are present in the precipitate after fragmentation and that can contribute a "chalky" or "gritty" texture to the dispersion. Treatment of the heated suspension/solution of the precipitate with acid or enzyme to hydrolyze a substantial portion of the soluble fraction can reduce or eliminate such large particles. Typical treatment conditions will involve mild hydrolysis catalyzed by acid, e.g. in a solution of 0.1N HCl for one hour, or, preferably, by enzyme, e.g. $\alpha$-amylase.

The isolated debranched amylopectin starch precipitate is typically washed and then dried (e.g. to a low moisture content, typically 3–8%) after isolation to allow for handling and storage prior to further processing. Examples of drying techniques include spray drying, flash drying, tray drying, belt drying, and sonic drying. The dried precipitate may be hygroscopic. Thus, some rehydration during handling and storage may occur. Depending upon the precise composition of the precipitate and the conditions (including length of time) of storage, steps to maintain the moisture at a low content may be necessary (e.g. moisture barrier packaging and/or control of humidity in the storage environment). If the moisture content is allowed to rise too far (e.g. greater than about 20%, or possibly greater than 15%), bulk handling problems and/or microbiological stability problems might arise.

The debranched amylopectin starch precipitate may also be otherwise chemically modified. Examples of such chemical modification include the product of reaction with bleaching agents (e.g. hydrogen peroxide, peracetic acid, ammonium persulfate, chlorine (e.g. calcium and/or sodium hypochlorite or sodium chlorite), and permanganate (e.g. potassium permanganate)); esterifying agents (e.g. acetic anhydride, adipic anhydride, octenyl succinic anhydrides, succinic anhydride, vinyl acetate); including phosphorous compounds (e.g. monosodium orthophosphate, phosphorous oxychloride, sodium tripolyphosphate, and sodium trimetaphosphate); and/or etherifying agents (e.g. acrolein, epichlorohydrin, and/or propylene oxide). Such chemical modifications will typically be accomplished after the debranching step, but may be accomplished prior to the debranching or effected by using a modified starch as a starting material for the debranching step, provided such modification does not preclude debranching.

The debranched amylopectin starch precipitate is subjected to a physical fragmentation as by mechanical disintegration, i.e. fragmented. The degree of fragmentation will be sufficient to allow the precipitate to form a particle gel in an aqueous medium. Certain steps can be taken prior to fragmentation to enhance the susceptibility of the precipitate to fragmentation. For example, the addition to the solution of additives which will introduce imperfections into the crystalline structure of the precipitate, e.g. higher saccharides such as maltodextrins, may make the precipitate easier to fragment to the desired degree. Subjecting a slurry of the precipitate to mild hydrolysis catalyzed by acid, e.g. in a solution of 0.1N HCl for one hour, or, preferably, by enzyme, e.g. $\alpha$-amylase, may also make fragmentation easier.

The mechanical disintegration of the precipitate may be carried out in several ways, as by subjecting it to attrition in a mill, or to a high speed shearing action, or to the action of high pressures. Disintegration is generally carried out in the presence of a major amount by weight of a liquid medium, preferably water. Although tap water is the preferred liquid medium for the dispersion of fragmented starch precipitate, other liquids are suitable provided sufficient water is present to hydrate the fragmented starch precipitate and, thus, result in a dispersion having the characteristics of a particle gel. Sugar solutions, polyols, of which glycerol is an example, alcohols, particularly ethanol, isopropanol, and the like, are good examples of suitable liquids that can be in admixture with water in the liquid medium. It may also be possible to fragment the starch precipitate in a non-hydrating medium (e.g. 95% ethanol), then solvent exchange with water, and finally redisperse the fragmented starch precipitate to form an aqueous dispersion. Typically, however, the starch precipitate will be physically fragmented in potable water.

The mechanical disintegration is preferably accomplished by subjecting an aqueous dispersion of the precipitate to high shear, e.g. in a Waring blender or a homogenizer such as that disclosed in U.S. Pat. No. 4,533,254 (Cook et al.) and commercially available as a MICROFLUIDIZER TM from Microfluidics Corporation, Newton, Mass., or a homogenizer such as the RANNIE TM high pressure laboratory homogenizer, Model Mini-lab, type 8.30H, APV Rannie, Minneapolis, Minn. Homogenizers useful in forming suspensions or emulsions are described generally by H. Reuter, "Homogenization", *Encyclopedia of Food Science*, pp. 374–376, (M. S. Peterson and A. H. Johnson, eds., AVI Publ. Co., Westport, Conn., 1978), L. H. Rees and W. D. Pandolfe, "Homogenizers", *Encyclopedia of Food Engineering*, pp. 467–472 (C. W. Hall et al., eds., AVI Publ. Co., Westport, Conn., 1986), and W. C. Griffin, "Emulsions", *Encyclopedia of Chemical Technology*, Vol. 8, pp. 900–930 (Kirk-Othmer, eds., John Wiley & Sons, Inc., New York, N.Y., 3d ed., 1979), the disclosures of which are incorporated herein by reference.

The temperature of the starch precipitate during the fragmentation step should be maintained below the temperature at which a major portion of the precipitate will dissolve in the aqueous medium. Thus, it may be desirable to cool the precipitate during disintegration. Alternatively, heat produced during fragmentation may cause the precipitate to dissolve, but cooling may cause the dissolved precipitate to reprecipitate and form a useful product. Whatever method is used, the disintegration is carried out to such an extent that the resulting finely-divided product is characterized by its ability to form a particle gel in the liquid medium in which it is attrited or in which it is subsequently dispersed.

The debranched amylopectin starch particles which make up the particle gel can be analyzed in a variety of ways. Rheological measurements can be made to determine the rheological characteristics of the resulting dispersion. Typically, the aqueous dispersion of debranched amylopectin starch particles will exhibit a transition in dynamic elastic modulus (G') versus shear strain at less than about 50 millistrain, and preferably less than about 10 millistrain, said transition being from a substantially constant G' versus shear strain to a decreasing G' versus shear strain. The transition indicates fracture of the particle network within the particle gel and is typically a sharp transition.

Analysis of the debranched amylopectin starch particles formed after dissolution shows that the starch has a measurable crystallinity. The crystalline regions of particles derived from fully debranched waxy maize starch (essentially no amylose component) exhibit a diffraction pattern characteristic of a starch material consisting essentially of A-type starch crystals. The crystalline regions of particles derived from substantially fully debranched common corn starch (about 28% amylose) exhibit a diffraction pattern characteristic of a starch material consisting essentially of B-type starch crystals.

It should also be noted that mechanical disintegration may be sufficient to produce an aqueous dispersion having the desired particle gel characteristics, but still leave a sufficient number of particles of sufficient size to exhibit a "particulate" or "chalky" mouthfeel when ingested. Such chalkiness can be reduced by the mild hydrolysis discussed above or by reducing the particle size of the starch precipitate before, during or after mechanical disintegration so that substantially all (typically at least about 95%, preferably at least 99%) of the precipitate will pass a U.S. #325 mesh sieve (i.e. substantially all particles are less than 45 microns). An example of a milling device suitable for such size reduction is a TROST TM Air Impact Mill from Gatlock, Inc., Newton, Pa.

The use of the fragmented, debranched amylopectin starch precipitate allows for the replacement of a substantial portion (e.g. from 10% to 100% by weight) of the fat and/or oil in a food formulation. The precise level of replacement that is possible without significantly decreasing the organoleptic quality of the food will generally vary with the type of food. For example, in a French-style salad dressing, it is generally possible to completely replace the oil component that is normally present. In other types of foods, e.g. frostings, icings, cream fillings, ice cream, margarine, etc., a major amount of the fat and/or oil (e.g. about 50% to about 80%) can be replaced with little effect on the organoleptic desirability of the food. Examples of typical foods in which fat and/or oil can be replaced include frostings (e.g. icings, glazes, etc.), creme fillings, frozen desserts (e.g. ice milk, sherbets, etc.), dressings (e.g. pourable or spoonable salad and/or sandwich dressings), meat products (e.g. sausages, processed meats, etc.), cheese products (e.g. cheese spreads, processed cheese foods), margarine, fruit butters, other imitation dairy products, puddings (e.g. mousse desserts), candy (e.g. chocolates, nougats, etc.), and sauces, toppings, syrups and so on.

Generally, it will be desirable to remove sufficient fat from a given food formulation to achieve a reduction in calories of at least one-third per customary serving or make a label claim of "cholesterol-free". (In this regard, see, for example, the list of standard serving sizes for various foods published in Food Labelling; Serving Sizes, 55 Fed. Reg. 29517 (1990) (to be codified at 21 C.F.R. 101.12), the disclosure of which is incorporated herein by reference, and the restrictions on labelling "cholesterol-free" at Food Labelling; Definitions of the Terms Cholesterol Free, Low Cholesterol and Reduced Cholesterol, 55 Fed. Reg. 29456 (1990)). It should also be noted that the fat removed from a particular formulation may be replaced with an equal amount by weight of an aqueous dispersion of fragmented starch precipitate, but that such equality may not be necessary or desirable in all instances. Further, it may be desirable to remove fat and add another ingredient (e.g. a gum, polydextrose, a protein, etc.) along with the aqueous dispersion of starch precipitate.

While this invention is generally directed to the replacement of fat and/or oil in a food formulation, it is of course within the contemplation of this invention that a fragmented, debranched amylopectin starch precipitate will be used in an entirely new formulation to which it contributes fat-like organoleptic qualities but is not, in the strictest sense, replacing a pre-existing fat or oil ingredient. Moreover, it is contemplated that the fragmented, debranched amylopectin starch precipitate will have utility as a thickener, bodying agent, or the like in foods that normally do not have a significant fat or oil component.

In general, the fragmented, debranched amylopectin starch precipitate is incorporated into the food as an aqueous dispersion, typically comprised of a major amount (i.e. greater than 50% by weight) of water or other liquid medium and a minor amount (i.e. less than 50% by weight, typically 10% to 40%) of starch precipitate solids. Alternatively, the isolated precipitate can be mixed with the food along with water and then subjected to disintegration in those instances when the other ingredients of the food are capable of withstanding the condition of disintegration, e.g. a salad dressing or imitation sour cream.

It is contemplated that commercial production and use may involve hydrolysis, mechanical disintegration, and drying (e.g. spray drying) of the fragmented starch precipitate to produce an item of commerce. This item of commerce will then be purchased by a food processor for use as an ingredient. To incorporate the dried, fragmented, debranched amylopectin starch precipitate into a food product, it may be useful and/or necessary to further mechanically disintegrate the starch precipitate while dispersing it into the foodstuff in which it will be employed. However, the techniques employed for such mechanical disintegration should not need to be nearly as vigorous as the original mechanical disintegration prior to drying.

The fragmented, debranched amylopectin starch precipitate can generally be heated while in a food system to dissolve a substantial portion of the precipitate. It appears that upon cooling, the precipitate undergoes reprecipitation and the resulting food product displays acceptable organoleptic properties. In some food systems, however, reprecipitation of the precipitate may be inhibited or modified, i.e. by the presence of an ingredient that can interact with the solubilized precipitate. If undesirable reprecipitation will occur, the fragmented, debranched amylopectin starch precipitate should not be subjected to conditions (e.g. elevated temperature) which will cause tile precipitate fragments (i.e. a majority by weight thereof) to dissolve.

Accordingly, if the food formulation is to be cooked or otherwise heated, to temperatures sufficient to dissolve the precipitate, such heating should be completed prior to the addition of the precipitate to the food. It should be noted, however, that in many foods that are cooked, e.g. cheesecake, the internal temperature and/or moisture availability may be insufficient to dissolve the starch precipitate fragments.

As noted above, the terms "food" and "foodstuffs" are intended broadly, as relating to both nutritional and/or functional food ingredients. It is contemplated that one or more food ingredients may be mixed with the aqueous dispersion of fragmented, debranched amylopectin starch precipitate, or even dry mixed with the debranched amylopectin starch precipitate prior to mechanical disintegration.

Among the food ingredients in the food formulations of this invention include flavors, thickeners (e.g. starches and hydrophilic colloids), nutrients (e.g. carbohydrates, proteins, lipids, etc.), antioxidants, antimicrobial agents, non-fat milk solids, egg solids, acidulants, and so on.

Hydrophilic colloids can include natural gum material such as xanthan gum, gum tragacanth, locust bean gum, guar gum, algin, alginates, gelatin, Irish moss, pectin, gum arabic, gum ghatti, gum karaya and plant hemicelluloses, e.g. corn hull gum. Synthetic gums such as water-soluble salts of carboxymethyl cellulose can also be used. Starches can also be added to the food. Examples of suitable starches include corn, waxy maize, wheat, rice, potato, and tapioca starches.

Non-fat milk solids which can be used in the compositions of this invention are the solids of skim milk and include proteins, mineral matter and milk sugar. Other proteins such as casein, sodium caseinate, calcium caseinate, modified casein, sweet dairy whey, modified whey, and whey protein concentrate can also be used herein.

For many foods, it is accepted practice for the user to add the required amount of eggs in the course of preparation and this practice may be followed just as well herein. If desired, however, the inclusion of egg solids, in particular, egg albumen and dried yolk, in the food are allowable alternatives. Soy isolates may also be used herein in place of the egg albumen.

Dry or liquid flavoring agents may be added to the formulation. These include cocoa, vanilla, chocolate, coconut, peppermint, pineapple, cherry, nuts, spices, salts, flavor enhancers, among others.

Acidulants commonly added to foods include lactic acid, citric acid, tartaric acid, malic acid, acetic acid, phosphoric acid, and hydrochloric acid.

Generally, the other components of the various types of food formulations will be conventional, although precise amounts of individual components and the presence of some of the conventional components may well be unconventional in a given formulation. For example, the conventional other components for foods such as frozen desserts and dressings, are described in European Patent Publication No. 0 340 035, published Nov. 2, 1989 (the pertinent disclosure of which is incorporated herein by reference), and the components and processing of table spreads is disclosed in U.S. Pat. No. 4,869,919 (Lowery), the disclosure of which is incorporated by reference.

A particularly advantageous use of the fragmented starch precipitates described herein may be the use thereof to replace a portion of the shortening used in a layered pastry article. In layered pastry articles (Danish, croissants, etc.) layers of a bread dough are assembled with a "roll-in" placed between the layers. The roll-in commonly contains a "shortening" (i.e. a fat and/or oil component) from an animal (e.g. butter) or vegetable (e.g. partially hydrogenated soybean oil) source. The assembled article, optionally containing a filling or topping, is then baked to form a finished pastry. At least a portion of the shortening of an otherwise conventional roll-in can be replaced with an aqueous dispersion of fragmented, debranched amylopectin starch precipitate, preferably in admixture with an emulsifier (e.g. mono- and/or di-glycerides), and used to make a layered pastry.

The following examples will illustrate the invention and variations thereof within the scope and spirit of the invention will be apparent therefrom. All parts, percentages, ratios and the like are by weight throughout this specification and the appended claims, unless otherwise noted in context.

EXAMPLES

Example 1

A totally debranched, waxy maize starch precipitate was prepared and fragmented as follows. Into a 3-liter stainless steel beaker was placed 2000 grams of aqueous slurry containing 5% dry solids waxy corn starch. The pH was adjusted to 4.5 using 0.5N HCl and the beaker was placed in a 95° C. water bath. The slurry was stirred and allowed to gelatinize and heat at 93°–95° C. for 20–30 minutes. The major portion of the resulting waxy starch paste (1150 grams paste) was placed into a pressure reactor and heated to 160° C. with stirring. After stirring at 160° C. for 30 minutes, the waxy starch solution was cooled to 45° C. and transferred to a 2-liter 3-neck round bottom flask equipped with stirrer, thermometer and a temperature controlled water bath. To the flask at 45° C. and pH 4.5 was added 50 units isoamylase enzyme (Sigma Chemical Co., St. Louis, Mo.) per gram dry basis of starch. The enzyme reaction was allowed to proceed with stirring at 45° C. for 48 hours. At the end of this period, the solution was heated to boiling (approximately 100° C.) to inactivate enzyme then cooled and evaporated to 20% solids using a rotary evaporator.

The resulting solution was allowed to set in a refrigerator to precipitate/crystallize. The resulting slurry was centrifuged at about 10,000 g-force RCF in a Sorvall Centrifuge (GSA rotor) for 20 minutes. The supernatant was decanted. The sediment was resuspended in water to the original 20% solids concentration volume, heated to boiling then cooled and again allowed to precipitate/crystallize on standing in a refrigerator. The resulting slurry was centrifuged as before and the sediment dried at 50° C. on a stainless tray in a forced air oven. The yield of product was calculated to be 81.3% on a dry basis.

Three additional samples were prepared in a similar manner with minor variations in treatment. Portions of all four samples were combined and heated to boiling to solubilize almost all material present in the 20% solids preparation. The hot solution was filtered through Whatman No. 1 filter paper on a (Buchner funnel and the clear filtrate was placed in a refrigerator overnight to precipitate/crystallize. The resulting mass was filtered using Whatman No. 1 filter paper on a Buchner funnel and the precipitated mass was washed with additional water. The resulting wet cake was dried on a stainless steel tray overnight in a forced air oven at 50° C. The dried product was ground to pass through a US #60 mesh sieve and bottled.

Into a 250 ml 3-neck round bottom flask was placed 65.0 grams of the dried product above (57.5 grams dry basis) and 106.7 grams of acidic aqueous solution containing 3.87 grams of 100% HCl (approximately 1N HCl solution). The mixture was heated to 60° C. in a water bath and stirred at 60° C. for 24 hours. The mixture was adjusted to pH 4.5 with 4% NaOH and then centrifuged. The supernatant was discarded and the sediment resuspended in the same volume of water and centrifuged again. The wet cake was dried in a forced air oven.

A 20.0% solids creme of the above product was prepared by simply blending at full speed in a Waring blender at 60° C. for approximately 8 minutes with the temperature controlled. Yield stress of the creme was found to be 522 pascals. The creme had a very smooth consistency and excellent body when rubbed between the finger and thumb. Based on our experience, this product would make a good fat replacer.

Example 2

A totally debranched common (dent) corn starch was prepared by enzymatic hydrolysis with isoamylase. The liquefaction of the starch involved heating a 5% d.s. starch slurry to 95° C. and holding it for 20 minutes. The hot slurry was placed into a Bomb reactor and heated to 160° C. The liquefied starch was vented through a cooling coil to a 3-neck flask equipped with a Servodyne mixer and contained in a 45° C. circulating bath.

The liquefied starch was then prepared for the enzyme hydrolysis. The pH was adjusted to 4.5 with 1N HCl and the temperature of the slurry was allowed to reach 45° C. The isoamylase (Hayashibara) was added to the slurry at 100 units per gram dry basis of the starch. After 24 hours, the reaction slurry was heated to greater than 80° C. for 20 minutes to inactivate the enzyme. The slurry was concentrated to 20% d.s. on a rotoevaporator. The resulting solution was placed in a beaker, covered, and allowed to crystallize overnight at refrigerated temperature. The resulting material was centrifuged at 10,000 rpm for 20 minutes. The supernatant was decanted and the pellet resuspended to the original weight. This slurry was recrystallized by heating to greater than 90° C. and refrigerating overnight. The crystallized material was spread on a stainless steel tray and dried at 50° C. The dried material was ground so that it would pass a U.S. #60 mesh screen.

The dried totally debranched starch material was sheared at 60° C. for 8 minutes in a Waring blender. The resulting dispersed material had a fat-like lubricating property and a yield stress of 211 Pa. The yield stress and texture were similar to our first debranching of the waxy maize starch.

Example 3

A totally debranched waxy maize starch was prepared by enzymatic hydrolysis with isoamylase (Hayashibara). A 20% d.s. slurry of waxy maize starch was jet cooked at 310° F. and 60 psi. A portion of the resulting liquefied starch was placed into a 3-neck round bottom flask equipped with a stirrer, thermometer and a 45° C. temperature controlled water bath. The pH of the slurry was adjusted to 4.5 with 1N HCl. The isoamylase enzyme was added to the slurry at 200 units per gram dry basis of the starch., After 48 hours, the reaction slurry was heated to greater than 80° C. for 20 minutes to inactivate the enzyme. The resulting solution was placed into a beaker, covered and allowed to crystallize overnight at refrigerated temperatures. The resulting material was heated to 95° C. and left to recrystalize at refrigerated temperatures overnight. The recrystallized material was then spread on a stainless steel tray and dried overnight at 50° C. The material was ground to a fine powder on a TROST mill and sieved through a 38 micron screen.

The resulting powder of the precipitate from above was prepared as a 30% d.s. creme for use in making a reduced fat sour cream. The creme preparation involved making a 30% d.s. slurry of the precipitate and heating it to 75° C. The hot slurry was sheared in a MICROFLUIDIZER using module 1351 and 15,000 psi. The resulting creme was incorporated into the following reduced fat sour cream formula:

| Ingredients: | % |
|---|---|
| Precipitate (30% d.s. creme) | 39.79 |
| Sour cream | 29.83 |
| Water | 23.41 |
| Non-fat dry milk | 5.97 |
| Lactic acid 88% | 0.40 |
| Xanthan gum | 0.20 |
| Salt | 0.20 |
| Sodium citrate | 0.20 |
| Procedure: | |
| Lactic acid was added to the water and mixed well with a Kitchen Aide mixer. The dry ingredients were added and incorporated into the water making a slurry. The precipitate salve and the sour cream were blended into the slurry. The resulting material was hand homogenized and refrigerated. | |

The sour cream prototype made using the precipitate demonstrated good quality texture, appearance, and flavor.

Example 4

A totally debranched waxy maize starch precipitate was prepared and treated with α-amylase, before fragmentation, as follows. Into a Groen kettle was placed 25,400 grams of deionized water and 8,400 grams waxy maize starch (11.1% moisture) with stirring. The resulting slurry was jet cooked at 310° F. to give a 20% solids waxy maize starch paste.

Into a 5000 ml 3-neck round bottom flask was placed 3200 grams of the waxy maize starch paste above. The solution was agitated and the pH adjusted to approximately 4.2 with 1N HCl. With agitation at 1000 RPM, 128,000 units of isoamylase (Hayashibara) enzyme (200 units/gram dry starch) was added at 45° C. The reactor contents were allowed to react at 45° C. for 24 hours. The temperature was increased and the contents were heated at about 85° C. for about 25 minutes to inactivate the enzyme. The resulting solution was placed in a refrigerator where crystallization took place. The precipitated mass was heated to above 90° C. then allowed to set in the refrigerator overnight. The mass was then dried at 55° C. in a forced air oven. It was found by GPC chromatography that the product had 82% material less than 20,000 molecular weight.

Into a 2-liter glass beaker was placed 218 grams (200 grams dry basis) of the debranched waxy maize starch above, 16 grams of 1M phosphate buffer and 766 grams deionized water giving a 20% suspension in 20 millimolar phosphate buffer. The suspension was heated to about 100° C. (boiling) to dissolve most starch then cooled to 25° C. to give freshly precipitated/crystallized material.

To one half of the above freshly precipitated material, with the pH adjusted to 6.9, with agitation was added 1500 units (51 microliters) of porcine pancreatic α-amylase (Sigma Chemical Co. #A 6255) and the mixture was allowed to react at 25° C. for 24 hours. The slurry tended to thin out and stirred better with time. After 24 hours, the mixture was slowly mixed with 8 volumes of ethanol to precipitate the solids and inactivate the α-amylase enzyme. The alcohol precipitated slurry was centrifuged at 5000×g for 10 minutes and the sediment was dried first in air then in a vacuum oven at approximately 1.5 mm Hg and 50° C. overnight. The resulting product was ground to pass through a US #60 mesh sieve then bottled and labeled.

A 20.0% solids slurry of the above product was sheared using a small Waring blender with temperature controlled water jacket (e.g. 120 V, 60° C., 8 ½ minutes). After setting 3 hours, the yield stress was measured and found to be 408 pascals. On tasting, the texture was found to be creamier with no chalkiness of a similar preparation that had not been treated with α-amylase. Based on our experience, this product would be useful as a fat replacer. CL EXAMPLE 5 into a 3-liter, 3-neck round bottom flask equipped with stirrer, thermometer and temperature regulated water bath was placed 2200 grams of 5% solids gelatinized waxy maize starch paste, previously heated to 96° C. for 30 minutes, heated to 160° C. for 30 minutes, then cooled to room temperature. To the waxy maize paste at pH 6.6 was added 11,000 units (100 units/gram dry starch) of Novo Nortek Promozyme Pullulanase Enzyme. The mixture was stirred and maintained at 58°-60° C. for 24 hours. Samples were taken at 6 hour, 18 hour, and 24 hour reaction periods, heated to about 90° C. for about 10 minutes to inactivate enzyme, then freeze dried and analyzed by gel permeation chromatography (GPC) molecular weight.

After 24 hours, the reaction mixture was heated to about 90° C. to inactivate enzyme and the hot solution filtered through Whatman #2 filter paper in a Buchner funnel. The slurry was concentrated via rotary evaporator to 20% solids, then placed into a refrigerator at 4° C. overnight.

The resulting precipitated mixture was centrifuged and the supernatant discarded. The sediment was resuspended in an equal volume of water, heated to about 90° C. and allowed to precipitate in a refrigerator at 4° C. overnight. The precipitated mixture was centrifuged and the supernatant was discarded. The sediment was dried on stainless steel trays at 35° C. overnight. The dried product was ground to pass through a US #60 mesh sieve. Gel permeation chromatography (GPC) analytical results are reported below.

| Reaction Time (hr) | $M_w$ | $M_n$ | $M_w/M_n$ | Peak Molecular Weights | Per Cent Less Than 20,000 Molecular Weight |
|---|---|---|---|---|---|
| 6 | 15,400 | 1,186 | 12.9 | 75,224;2556;335 | 87.5 |
| 18 | 7,900 | 1,074 | 7.3 | 64,412;2637;335 | 94.3 |
| 24 | 6,747 | 1,014 | 6.7 | 62,000;2772;345 | 95.2 |

If a finding of >80% saccharities having less than 20,000 molecular weight is considered as substantially completely debranched then it can be seen that complete debranching was achieved using pullulanase enzyme.

Examples 6-13

A series of debranched starch products were prepared from waxy maize starch under conditions similar to those employed in Examples 1 or 5, with isoamylase or pullulanase, respectively. Variations in conditions employed and results are shown in Table 1.

and fragmented as 25% precipitate solids in water to form a creme.

The strain sweep experiments were conducted with the creme products at 1 Hz frequency using a concentric cylinder geometry. During the test, strain was increased by changing oscillation amplitude and the dynamic elastic modulus (G') was measured as a function of strain.

The G' values correspond to the strength of the network structure in the creme. The creme displays linear viscoelasticity at very low strains., i.e. G' is independent of strain. Its behavior becomes non-linear (G' decreases as strain increases) at a certain critical strain where the material structure becomes more "deformable". A short or brittle material will display a transition from linear to non-linear viscoelasticity at a lower strain. If the transition occurs at a higher strain, this indicates a long and cohesive texture.

It can be seen from FIG. 1 that at 57% debranching (Curve A) there is no break in structure observed even at high strain. At about 69% debranching (Curve B), a break in structure is observed at about 10 millistrain. At about 85% (Curve C) and higher debranching (100%, Curve D), we can see structure breakdown at less than about 1 millistrain which is closer to the value (Curve E) observed for a commercially available brand of hydrogenated shortening (i.e. CRISCO TM, Procter & Gamble Co., Cincinnati, Ohio).

In general, particle gel compositions deform at low strain values and usually do so with large changes in G' values. By contrast, polymer network gels usually deform at high strain values and typically display relatively low changes in G' values.

TABLE 1

| | EXAMPLE | | | | | | | |
|---|---|---|---|---|---|---|---|---|
| | 6 | 7 | 8 | 9 | 10 | 11 | 12 | 13 |
| % Conversion | 93 | 96 | 82 | 85 | 100 | 57 | 57 | 69 |
| Debranching enzyme (P - pullulanase) (I - isoamylase) | P | P | I | I | I | P | P | P |
| % Cold water solubles, powder | 31.7 | 37.7 | 21.4 | 30.6 | 24.7 | 34.4 | 99.2 | 29.6 |
| Yield stress, pascals | 118 | 17 | 498.5 | 1110 | 428 | Too gelled | Too gelled | Too gelled |
| % Cold water solubles, creme (gel) | 25.5 | — | — | — | — | — | 13.8 | 11.5 |
| DSC: | | | | | | | | |
| Onset °C. | 54 | 47 | 45 | — | 57 | — | 43 | 47 |
| Enthalpy | 13.8 | 21.3 | 23.6 | — | 20.6 | — | 9.5 | 29.3 |
| Water immobilization (sec$^{-1}$ by $^{17}$O NMR) | 119 | 115 | 697 | — | — | — | 209 | 353 |
| Ratio of 1,4:1,6 linkages (by NMR) | >400/1 | * | 110/1 | — | — | 31/1 | 31/1 | 120/1 |
| Concentration of starch (during hydrolysis) | 20 | 5 | 20 | 20 | 5 | 20 | 20 | 20 |
| Units of enzyme (per g starch) | 62.5 | 100 | 200 | >200 | 100 | 3.79 | 3.79 | 7.5 |
| Number of precipitations | 2 | 2 | 2 | 2 | 2 | 1 | 0 | 2 |
| Centrifugation | Yes | Yes | No | No | No | No | No | No |

*No α-1,6 linkages detected

Example 14

Dynamic strain sweep evaluations were performed using a model VOR Bohlin Rheometer on sheared waxy maize starch products debranched to varying degrees from 57% to 100% (e.g. 57% to 100% of the products had a molecular weight of less than 20,000

Example 15

Two experiments were conducted whereby waxy maize starch was first jet cooked, cooled and debranched with isoamylase enzyme. Then, using a programmable waterbath, the 15% solids debranched starch solutions were subjected to multiple heating and cooling cycles to promote formation of increasing quantities of thermostable crystalline product.

Thus, 3,507 grams of 15% dry solids waxy maize starch paste previously jet cooked using typical conditions (310° F. and 80 lbs. steam) was adjusted to pH 4.5 and reacted with 200 units isoamylase enzyme (Hayashibara) per gram of starch at 45° C. in a 5-liter, 3-neck round bottom flask for 66 hours. Gel permeation chromatography analysis showed 100% debranching (i.e. 100% of the material was less than 20,000 molecular weight).

After heating to inactivate the enzyme, the solution of debranched waxy maize starch was placed in a waterbath equipped with programmable heating and cooling capabilities. The waterbath heated the flask contents to 99° C. and held it there for 60 minutes then cooled to 4° C. and held at that temperature for 60 minutes. The cycle of heating and cooling were repeated a total of eight times. Samples of product suspension were withdrawn periodically during the heat treatment, dried, ground and analyzed for crystallinity via differential scanning calorimetry (DSC). The results are presented in Table 2.

TABLE 2

DSC Analysis of 100% Debranched Waxy Maize Starch Crystallized During Multiple Cycling of Temperature from 99° C. to 4° C.

| Number of Crystallization Cycles Completed | Melting Onset Temp °C. | Melting End Temp °C. | Total Enthalpy J/g | Enthalpy <75° C. % | Enthalpy >75° C. % |
| --- | --- | --- | --- | --- | --- |
| 2 | 46 | 121 | 26 | 27 | 73 |
| 6 | 46 | 132 | 28 | 19 | 81 |
| 8 | 47 | 132 | 26 | 17 | 83 |

It can be seen from Table 2 that the percentage of product greater than about 75° C. in melting temperature reached a maximum (about 80% of the total crystalline material present) after about 6 heating/cooling cycles. This represents a high percentage of product with melting point above 75° C. Thus, it is possible that this product could be heated in water to 75° C. to solubilize the melted fraction while keeping the more stable (>75° C.) fraction intact. The two components could then be separated (e.g. by microfiltration) to give a new heat-stable product that is essentially all stable up to about 75° C.

From observation of the actual individual DSC scans whose results are summarized in Table 2, it was noted that the 100% debranched waxy maize starch product recrystallized by recycling from 99° C. to 4° C. formed a major peak centered at about 115° C. while reducing the size of the peak at about 85° C. as the number of crystallization cycles increased.

Another batch of waxy maize starch was jet cooked and debranched in a similar manner but at about 17% solids and for 48 hours, giving a product about 70% debranched. This product was cycled in a similar manner by heating to 75° C. and cooling to 25° C. After the final cycle, number 8, the product was split into two portions, one of which was analyzed without washing and the other, 8(w), was washed with water before analysis. These results are presented in Table 3. Another sample of this 70% debranched product was held at 75° C. without cycling for the time equal to 6 cycles; one portion was collected without washing (A) and a second portion was collected after a water wash (B).

TABLE 3

DSC Analysis of 70% Debranched Waxy Maize Starch Crystallized During Multiple Cycling of Temperature from 75° C. to 25° C.

| Number of Crystallization Cycles Completed | Melting Onset Temp °C. | Melting End Temp °C. | Total Enthalpy J/g | Enthalpy <75° C. % | Enthalpy >75° C. % |
| --- | --- | --- | --- | --- | --- |
| 1 | 48 | 102 | 22 | 48 | 52 |
| 2 | 49 | 105 | 19 | 31 | 69 |
| 6 | 42 | 109 | 19 | 54 | 46 |
| 8 | 48 | 111 | 16 | 47 | 53 |
| 8 | 49 | 108 | 17 | 47 | 53 |
| A | 49 | 100 | 20 | 54 | 46 |
| B | 47 | 92 | 21 | 47 | 53 |

In Table 3, it can be seen that the 70% debranched product appeared to reach a maximum percentage of more stable product (e.g. >75° C. melting point) after two heating/cooling cycles, but this did not appear to continue to be the case after additional cycles. The relatively low percentage of enzyme conversion no doubt contributed to this lower overall yield of stable product. In addition, the lower maximum temperature for heating also likely had a negative effect. From observation of the actual DSC scans, it was seen that the peak centered at about 95° C. increased with the number of heating cycles while the peak centered at about 75° C. decreased.

Overall, a high yield of thermostable product is achieved by cycling highly debranched waxy maize starch at relatively high temperature through at least two heating/cooling cycles.

Example 16

ACID HYDROLYSIS OF HEAT TREATED, DEBRANCHED 55% HIGH AMYLOSE CORN STARCH

A 2% solids slurry of 55% high amylose corn starch (HI-SET C) was prepared by mixing 452.3 grams (400 grams dry basis) of HI-SET C corn starch with deionized water to give a total volume of 20 liters. The suspension was heated in 2-liter batches up to 160° C. in a pressure reactor then cooled to about 30° C. to 50° C. by passing the hot solution through a cooled heat exchanger tube. The pH of the solution was adjusted to approximately 4.5 and the solution was placed in two 12-liter round bottom flasks equipped with agitation, condensers, and heat controlled water baths. The temperature was adjusted to 45° C. and 400 units per gram dry basis starch of isoamylase enzyme (from Hayashibara Co. and containing 865,000 units/gram) was added to each solution. The solutions were allowed to react 20 hours then the 2% solids solutions/dispersions (the debranched starch tends to precipitate with time) were heated to 160° C. in the pressure reactor as before to completely dissolve the precipitated starch and make it more readily available for isoamylase enzyme attack. The solutions were cooled, the pH again checked and found to be approximately 4.5, then 400 units per grams dry basis starch of isoamylase enzyme was again added and the reaction was allowed to proceed 18 hours at 45° C. for a total reaction time of 38 hours.

The 2% solution/suspension after 38 hours of isoamylase digestion was heated to approximately 95° C. to inactivate enzyme then concentrated by rotary evaporation over a 2-day period (stored in a refrigerator overnight) to approximately 15% solids. The slurry was dried on stainless steel trays at 60° C. in a forced air oven overnight and the dried material ground to pass through a US #60 mesh sieve.

To 380 grams (350 grams dry basis) of the above dried, screened material was added 1,720 grams of deionized water to give a 20% solids slurry. The slurry was heat treated by controlled heating in a temperature controlled water bath from 50° C. up to 100° C. at the rate of 0.05° C. per minute followed by controlled cooling from 100° C. down to 50° C. at the rate of 0.05° C. per minute. The heat treated slurry was poured onto a stainless steel tray and dried in a forced-air oven at 50° C. then ground to pass through a US #60 mesh sieve. This sample served as a substrate for acid hydrolysis treatments to improve the ease of creme formation on shearing.

The above starch substrate was acid hydrolyzed at 35% solids (a thick slurry) at 80° C. with an HCl solution of 0.14 Normality (includes all water and acid present in the slurry). Samples of reaction slurry were withdrawn after 6 hours, 12 hours, 18 hours and 24 hours of hydrolysis at 80° C., adjusted to pH 4.5, then tray dried at 50° C. and ground to pass through a US #60 mesh sieve. Additional samples hydrolyzed at 6 hours and 24 hours were washed to remove most solubles. The washing procedure followed diluting the reaction slurries approximately 50:50 with water then neutralizing with 5% NaOH. The neutralized slurries were centrifuged at 8000×g for 10 minutes and the supernatant discarded. Deionized water was added back to the sediment to give the same original weight of slurry and the sediment was dispersed uniformly in the water and centrifuged. This process was repeated two more times. The samples were then tray dried as outlined above. Finally, one sample hydrolyzed for 6 hours was washed as outlined above but not dried. It was saved in the wet state. All samples were then sheared using a laboratory Waring blender with a small jacketed jar at 20% solids, 120 volts, 60° C. for 8 ½ minutes. After setting for at least 3 hours, the yield stress values were measured using a Brookfield viscometer. The results are reported below:

| Acid Hydrolysis Time, hr. | Yield Stress of 20% Cremes, Pascals | | |
|---|---|---|---|
| | No Wash/ Separation | Washed | Washed But Not Dried |
| 0 | 36 | — | — |
| 6 | 233 | 550 | 731 |
| 12 | 277 | — | — |
| 18 | 289 | — | — |
| 24 | 211 | 615 | — |

Estimates of product yields based on dry substance recoveries from the experiments are 69.9% for the washed 6 hour hydrolysis sample, 99.4% for the no wash/separation 24 hour hydrolysis sample, and 60.5% for the washed 24 hour hydrolysis sample.

It can be seen that as the hydrolysis of the unwashed, unseparated samples continued there was a maximum yield stress value reached then a decline due to overhydrolysis and subsequent conversion into soluble saccharities that contribute nothing to yield stress values. The yield stress values of these unwashed, unseparated products were generally lower than the typical 400 to 600 pascals desired. If the relative amount of insolubles could be increased in the starting material then we would expect higher yield stress values for these unwashed, unseparated products.

For those products washed to remove soluble saccharities, the yield stress values were much higher and well within the desired range. For the sample that was washed but not dried, there was a considerable increase in yield stress. This would indicate that drying tends to reduce yield stress values.

It is concluded that acid hydrolysis is beneficial in increasing the ease of shearing of heat treated, debranched 55% high amylose corn starch.

Example 17

ALPHA-AMYLASE HYDROLYSIS OF HEAT TREATED, DEBRANCHED 55% AMYLOSE CORN STARCH

A 2% solids slurry of 55% high amylose corn starch (HI-SET C) was prepared by mixing 452.3 grams (400 grams dry basis) of HI-SET C corn starch with deionized water to give a total volume of 20 liters. The suspension was heated in 2-liter batches up to 160° C. in a pressure reactor then cooled to about 30° C. to 50° C. by passing the hot solution through a cooled heat exchanger tube. The pH of the solution was adjusted to approximately 4.5 and the solution was placed in two 12-liter round bottom flasks equipped with agitation, condensors, and heat controlled water baths. The temperature was adjusted to 45° C. and 400 units per gram dry basis starch of isoamylase enzyme (from Hayashibara Co. and containing 865,000 units/gram) was added to each solution. The solutions were allowed to react 20 hours then the 2% solids solutions/dispersions (the debranched starch tends to precipitate with time) were heated to 160° C. in the pressure reactor as before to completely dissolve the precipitated starch and make it more readily available for isoamylase enzyme attack. The solutions were cooled, the pH again checked and found to be approximately 4.5, then 400 units per gram dry basis starch of isoamylase enzyme was again added and the reaction was allowed to proceed 18 hours at 45° C. for a total reaction time of 38 hours.

The 2% solution/suspension after 38 hours of isoamylase digestion was heated to approximately 95° C. to inactivate enzyme then concentrated by rotary evaporation over a 2-day period (stored in a refrigerator overnight) to approximately 15% solids. This slurry was dried on stainless steel trays at 60° C. in a forced air oven overnight and the dried material ground to pass through a US #60 mesh sieve.

To 380 grams (350 grams dry basis) of the above dried, screened material was added 1,720 grams of deionized water to give a 20% solids slurry. The slurry was heat treated by controlled heating in a temperature controlled water bath from 50° C. up to 100° C. at the rate of 0.05° C. per minute followed by controlled cooling from 100° C. down to 50° C. at the rate of 0.05° C. per minute. The heat treated slurry was poured onto a stainless steel tray and dried in a forced air oven at 50° C. then ground to pass through a US #60 mesh sieve. This sample served as a substrate for α-amylose hydrolysis treatment to improve the ease of creme formation on shearing.

The above starch substrate was enzyme hydrolyzed at 20% solids (375 grams total slurry wt.) at 25° C. with 15 units/gram starch of porcine pancreatic α-amylase (Sigma Chemical Company). Samples of reaction slurry were withdrawn (125 grams each) after 8 hours, 21 hours, and 48 hours of hydrolysis and the pH adjusted to 3.5 to inactivate enzyme. The 8 hour and 21 hour samples were filtered on a Buchner funnel followed by washing with about 250 ml each with deionized water. The sample hydrolyzed 48 hours-would not filter (very, very slow) and was centrifuged (7000×g), the supernatant discarded, then deionized water added back to the original sample weight. After stirring to give a homogenous mixture, this slurry was centrifuged as above and the supernatant discarded. This procedure was repeated a final time. All wet cakes or sediment (from filtration or from centrifugation) were mixed with 8 volumes of ethanol (formula 3A) to denature any remaining enzyme. They were then either filtered or centrifuged one last time. The wet cakes and sediment were dried in a 50° C. forced air oven and ground to pass through a US #60 mesh sieve. The products were weighed and yields were calculated for each. Yield stress values were obtained on 20% solids cremes prepared by shearing at 120 volts, 60° C. for 8 ½ minutes with a Waring blender equipped with a small jacketed jar. The yield stress values were measured using a Brookfield viscometer after the cremes stood at least 3 hours at room temperature. The analytical results are reported below.

| α-Amylase Hydrolysis Time, hr. | Product Yield, % db | Yield Stress, Pascals |
|---|---|---|
| 0 | — | 36 |
| 8 | 87.0 | 288 |
| 21 | 84.2 | 348 |
| 48 | 80.9 | 365 |

It was noted that the texture of the 8 hour creme was the most gritty while the 48 hour sample was more creamy and less gritty. It is speculated that continued enzyme hydrolysis would continue to improve texture (less gritty) and increase yield stress values.

It was noted that the pH of the 48 hour hydrolyzed sample declined to 5.7 (from 6.9). It is likely that this was caused by undesirable fermentation to form organic acids. Such a large decline in pH likely also caused reduced enzyme hydrolysis activity compared to what may have occurred if the pH had remained at 6.9.

It is concluded that the enzyme hydrolysis gave considerable improvement in the shearability of the heat treated, debranched high amylose starch. In addition, it also resulted in improved smoothness of texture.

Example 18

THERMOSTABLE PULLULANASE ENZYME TREATMENT

A 55% amylose corn starch (HI-SET C) is made up to 25% solids then jet cooked at 160° C. with a retention time of 10 minutes at 160° C. then cooled to ~100° C. The pH of the solution is adjusted to pH 6.0.

Novo thermostable pullulanase enzyme, as described in WO 92/02614, is added at 50 units per gram of starch and the reaction is allowed to proceed at 100° C. for 24 hours at which time GPC analysis will show that less than 10% of the remaining amylose and amylopectin molecules are above about 100,000 molecular weight.

The debranched solution is treated with 3% w/w (weight by weight basis) of decolorizing carbon (based on starch dry substance weight) at 90° C. The colorless carbon treated solution is cooled to 5° C. for 16 hours to bring about crystallization. The crystallized mass is dried in a spray drier at 15% solids after dilution with water.

The spray dried material is made up to 20% solids and heated from 50° C. to 100° C. at 0.05° C./minute then cooled to 100° C. at 0.05° C./minute. The heat treated material is treated at 20% solids at 80° C. for 24 hours in 0.2N HCl then cooled to room temperature. The acidic slurry is adjusted to pH 4.5 with 10% NaOH and microfiltered to reduce the soluble saccharide content to less than 10% (measured at room temperature). The slurry is spray dried at about 15% solids to give a heat stable, shearable starch based fat replacer having a yield stress at 20% solids greater than 400 pascals.

What is claimed is:

1. A foodstuff having a reduced level of fat and/or oil comprising a mixture of a foodstuff and a fragmented, debranched amylopectin starch precipitate as a replacement for at least a substantial portion of the fat and/or oil of said foodstuff, said fragmented, debranched amylopectin starch precipitate being composed of more than about 80% by weight short chain amylose, and being capable of forming a particle gel in aqueous dispersion, and wherein at least about 95% of fragmented precipitate has a particle size of less than 45 microns.

2. A foodstuff of claim 1 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

3. A foodstuff of claim 1 wherein said debranched amylopectin starch is derived from starch from a variety of Zea mays.

4. A foodstuff of claim 1 wherein said debranched amylopectin starch is derived from a starch consisting essentially of amylopectin.

5. A foodstuff of claim 1 wherein said debranched amylopectin starch is derived from waxy maize starch.

6. A foodstuff of claim 1 wherein said debranched amylopectin starch is essentially free of amylopectin having a molecular weight in excess of 20,000 g/mol.

7. A method of formulating a foodstuff containing a fat and/or oil ingredient comprising replacing at least a substantial portion of said fat and/or oil ingredient with a fragmented, debranched amylopectin starch precipitate, said fragmented, debranched amylopectin starch precipitate being composed of more than about 80% by weight short chain amylose, and being capable of forming a particle gel in aqueous dispersions, and wherein at least about 95% of the fragmented precipitate has a particle size of less than 45 microns.

8. A method of claim 7 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

9. A method of claim 7 wherein said debranched amylopectin starch is derived from starch from a variety of Zea mays.

10. A method of claim 7 wherein said debranched amylopectin starch is derived from a starch consisting essentially of amylopectin.

11. A method of claim 7 wherein said debranched amylopectin starch is derived from waxy maize starch.

12. A method of claim 7 wherein said debranched amylopectin starch is essentially free of amylopectin having a molecular weight in excess of 20,000 g/mol.

13. A method of making a composition of matter useful in replacing fat and/or oil in a food formulation comprising physically fragmenting a minor amount of a debranched amylopectin starch precipitate in a major amount of an aqueous liquid, the degree of said physically fragmenting and the degree of debranching being sufficient to form a particle gel of said composition, wherein said debranched amylopectin starch is composed of more than about 80% by weight short chain amylose, and wherein at least about 95% of the fragmented precipitate has a particle size of less than 45 microns.

14. A method of claim 13 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

15. A method of claim 13 wherein said debranched amylopectin starch is derived from starch from a variety of Zea mays.

16. A method of claim 13 wherein said debranched amylopectin starch is derived from a starch consisting essentially of amylopectin.

17. A method of claim 13 wherein said debranched amylopectin starch is derived from waxy maize starch.

18. A method of claim 13 wherein said debranched amylopectin starch is essentially free of amylopectin having a molecular weight in excess of 20,000 g/mol.

19. An aqueous dispersion useful as a replacement for fats and/or oils comprising a major amount by weight of water and a minor amount by weight of a fragmented, debranched amylopectin starch precipitate, the degree of debranching and fragmentation of said precipitate being sufficient to form a particle gel of said composition, wherein said debranched amylopectin starch is composed of more than about 80% by weight short chain amylose, and wherein at least about 95% of the fragmented precipitate has a particle size of less than 45 microns.

20. An aqueous dispersion of claim 19 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

21. An aqueous dispersion of claim 19 wherein said debranched amylopectin starch is derived from starch from a variety of Zea mays.

22. An aqueous dispersion of claim 19 wherein said debranched amylopectin starch is derived from a starch consisting essentially of amylopectin.

23. An aqueous dispersion of claim 19 wherein said debranched amylopectin starch is derived from waxy maize starch.

24. An aqueous dispersion of claim 19 wherein said debranched amylopectin starch is essentially free of amylopectin having a molecular weight in excess of 20,000 g/mol.

25. A method of making a composition of matter useful in replacing fat and/or oil in a food formulation comprising:
  (a) getatinizing a starch having an amylopectin component;
  (b) debranching the amylopectin in said gelatinized starch in a (debranched) debranching medium to convert more than about 80% by weight of the amylopectin to short chain amylose and form a debranched amylopectin starch in said medium;
  (c) fragmenting a minor amount of said dried debranched amylopectin starch in a major amount of an aqueous liquid, said fragmenting being effective to form a particle gel of said composition, wherein at least about 95% of the fragmented debranched starch has a particle size of less than 45 microns.

26. A foodstuff having a reduced level of fat and/or oil, comprising a mixture of a foodstuff and a fragmented, debranched amylopectin starch precipitate as a replacement for at least a substantial portion of the fat and/or oil of said foodstuff;
  wherein at least about 95% of the fragmented precipitate has a particle size of less than 45 microns;
  wherein said debranched amylopectin starch is derived from waxy maize starch and is essentially free of amylopectin having a molecular weight in excess of 20,000 g/mol;
  wherein said fragmented, debranched amytopectin starch precipitate is composed of more than about 80% by weight short chain amylose, and is capable of forming a particle gel in aqueous dispersion, and
  wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

* * * * *

UNITED STATES PATENT AND TRADEMARK OFFICE
CERTIFICATE OF CORRECTION

Patent No.: 5,395,640

Dated: March 7, 1995

Inventors: Harris et al.

It is certified that error appears in the above-identified patent and that said Letters Patent is hereby corrected as shown below:

At column 1, line 11, after "abandoned." insert --This application is also a continuation-in-part of U.S. application Serial No. 07/908,728, filed July 6, 1992, which was a continuation of U.S. application Serial No. 07/578,994, filed September 6, 1990, now abandoned, which was a continuation-in-part of U.S. application Serial No. 07/483,208, filed February 20, 1990, now abandoned.--.

At column 14, line 50 after "replacer." delete "CL EXAMPLE 5".

At column 14, line 51, delete "into" and insert --EXAMPLE 5. Into--.

In claim 7, at column 22, line 49, "dispersions" should be --dispersion--.

In claim 25, at column 24, line 20, delete "(debrached)".

Signed and Sealed this

Eighteenth Day of July, 1995

Attest:

BRUCE LEHMAN

*Attesting Officer*       Commissioner of Patents and Trademarks